United States Patent
Liu et al.

(10) Patent No.: US 6,207,425 B1
(45) Date of Patent: Mar. 27, 2001

(54) BIDIRECTIONAL PCR AMPLIFICATION OF SPECIFIC ALLELES

(75) Inventors: Qiang Liu, Arcadia; Steve S. Sommer, Duarte, both of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/150,900

(22) Filed: Sep. 10, 1998

Related U.S. Application Data

(60) Provisional application No. 60/058,575, filed on Sep. 11, 1997.

(51) Int. Cl.$^7$ .................................................. C12P 19/34
(52) U.S. Cl. ............................................................ 435/91.2
(58) Field of Search ............................................. 435/91.2

(56) References Cited

U.S. PATENT DOCUMENTS

| | | | |
|---|---|---|---|
| 5,185,244 | * | 2/1993 | Wallace ..................................... 435/6 |
| 5,314,809 | * | 5/1994 | Erlich et al. ......................... 435/91.2 |
| 5,811,235 | * | 9/1998 | Jeffreys ..................................... 435/6 |

OTHER PUBLICATIONS

Sarkar, G. et al., "Characterization of Polymerase Chain Reaction Amplification of Specific Alleles", *Analytical Biochemistry*, 186, 64–68 (1990).
Sommer, S. S. et al., "A Novel Method for Detecting Point Mutations or Polymorphisms and Its Application to Population Screening for Carriers of Phenylketonuria", *Mayo Clin Proc*, 64:1361–1372 (1989).
Wetmur, J. G., "DNA Probes: Applications of the Principles of Nucleic Acid Hybridization", *Critical Reviews in Biochemistry and Molecular Biology*, 26(3/4):227–59 (1991).
Wu, D. Y. et al., "Allele–Specific Enzymatic Amplification of β–Globin Genomic DNA for Diagnosis of Sickle Cell Anemia", *Proc. Natl. Acad. Sci.*, 86:2757–60 (Apr. 1989).
Ye S. et al., "Allele Specific Amplification by Tetra–Primer PCR", *Nucleic Acids Research*, 20 (5), 1152 (1992).
Yoshitake S. et al., "Nucleotide Sequence of the Gene for Human Factor IX (Antihemophilic Factor B)", *Biochemistry*, 24: 3736–50 (1985).
Gibbs R. A. et al., "Detection of Single DNA Base Differences by Competitive Oligonucleotide Priming", *Nucleic Acids Research*, 17 (7), 2437–48 (1989).
Newton, C.R. et al., "Analysis of Any Point Mutation in DNA. The Amplification Refactory Mutation System (ARMS)", *Nucleic Acids Research*, 17 (7), 2503–16 (1989).
Nichols, W.C. et al., "Direct Sequencing of the Gene for Maryland/German Familial Amyloidotic Polyneuropathy Type II and Genotyping by Allele–Specific Enzymatic Amplification", *Genomics*, 5:535–40 (1989).
Ruano G. et al., "Direct Haplotyping of Chromosomal Segments From Multiple Heterozygotes via Allele–Specific PCR Amplification", *Nucleic Acids Research*, 17 (20), 8392 (1989).
Rychlik W. et al., "Optimization of the Annealing Temperature for DNA Amplification in vitro", *Nucleic Acids Research*, 18 (21), 6409–12, (1990).
Sarkar G. et al., "Double–Stranded DNA Segments Can Efficiently Prime the Amplification of Human Genomic DNA", *Nucleic Acids Research*, 20 (18), 4937–38 (1992).

* cited by examiner

*Primary Examiner*—Kenneth R. Horlick
(74) *Attorney, Agent, or Firm*—Rothwell, Figg, Ernst & Manbeck

(57) ABSTRACT

Bi-directional polymerase chain reaction (PCR) amplification of specific alleles (Bi-PASA). Two outer primers (P and Q) and two inner primers (A and B) are used. A and B are each specific for different alleles. In heterozygotes, three segments are amplified: a segment of size AQ resulting from one allele, another segment of size PB resulting from the second allele, and a combined segment of size PQ. In homozygotes, segment PQ and either segments AQ or PB amplify.

13 Claims, 6 Drawing Sheets

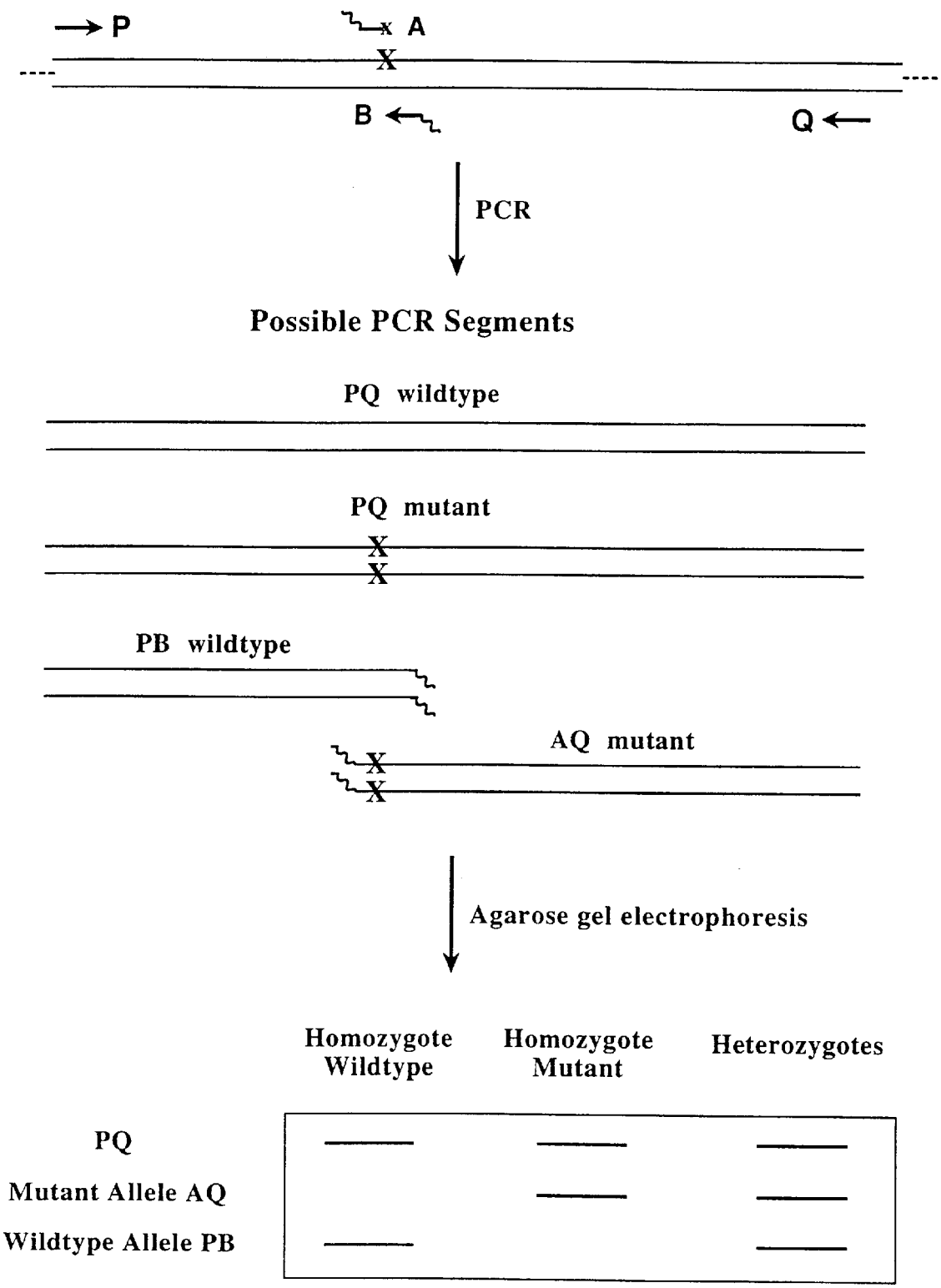

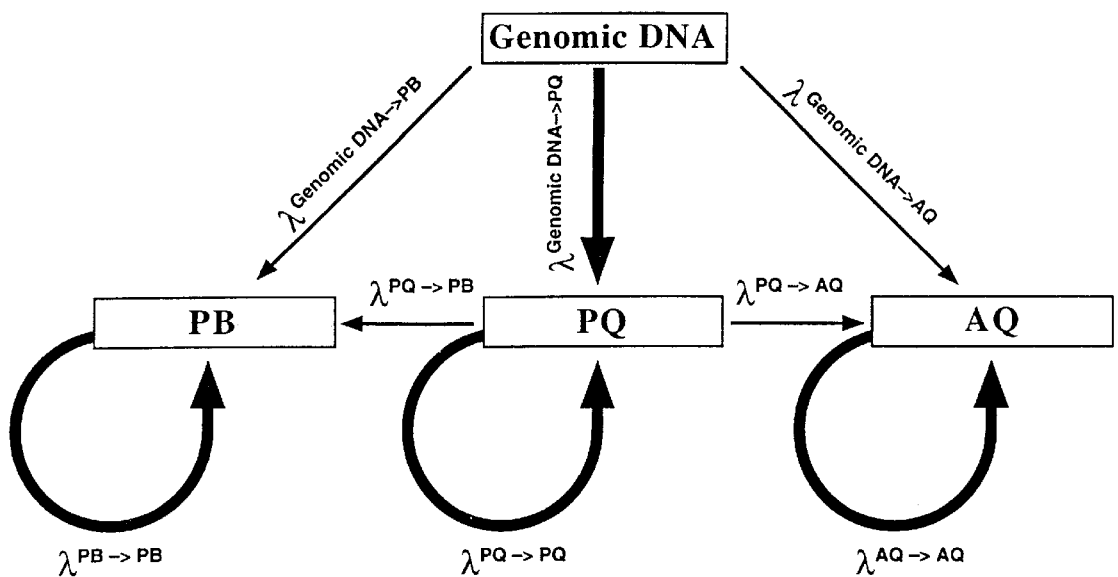
Fig 1B    Network Structure of Bi-PASA

Fig. 2
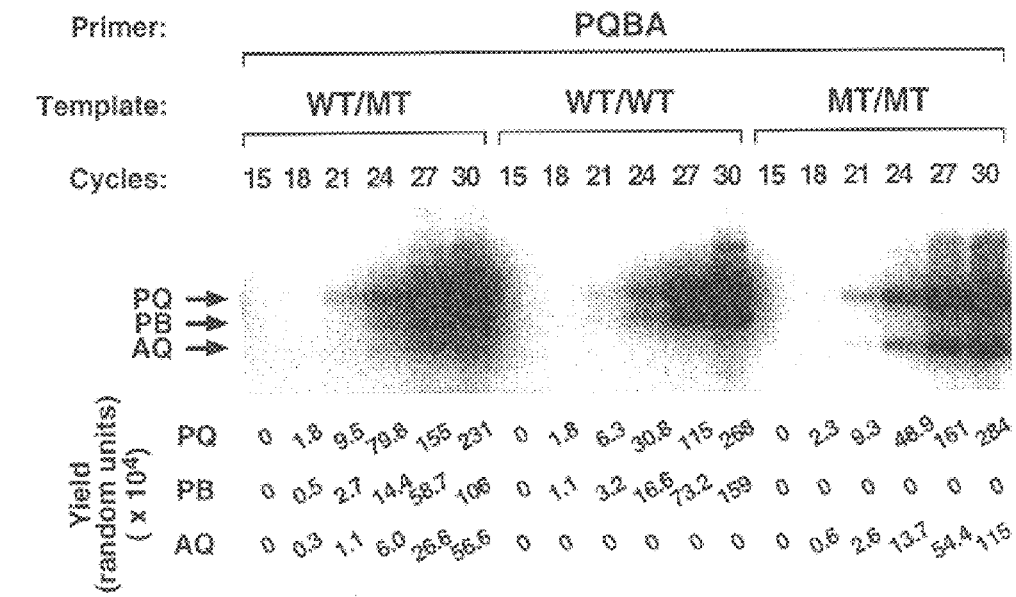
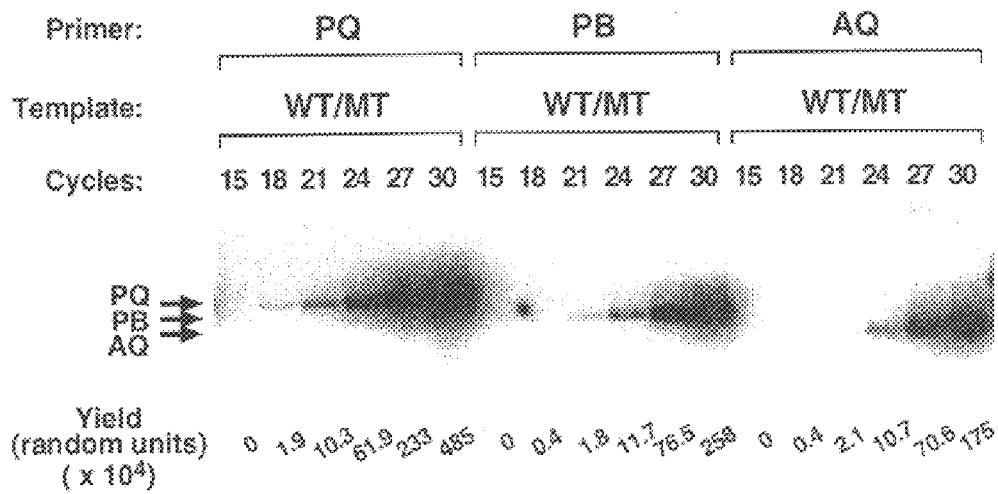

Fig.3
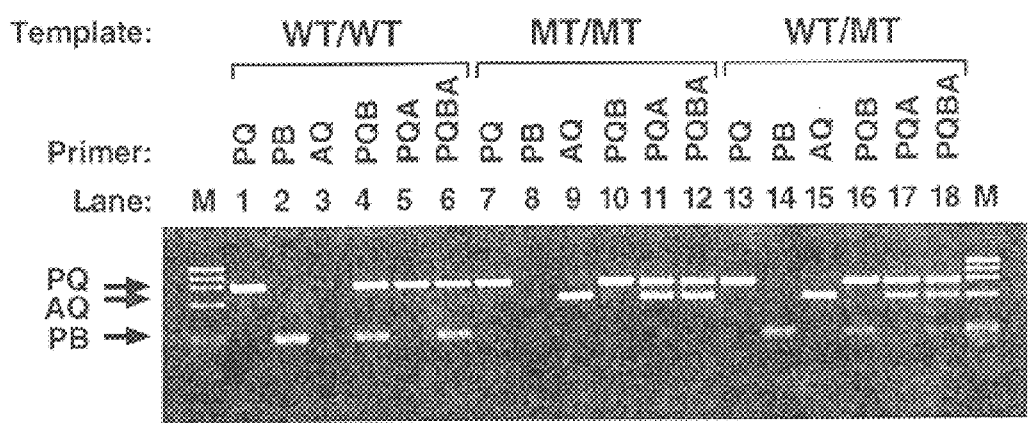
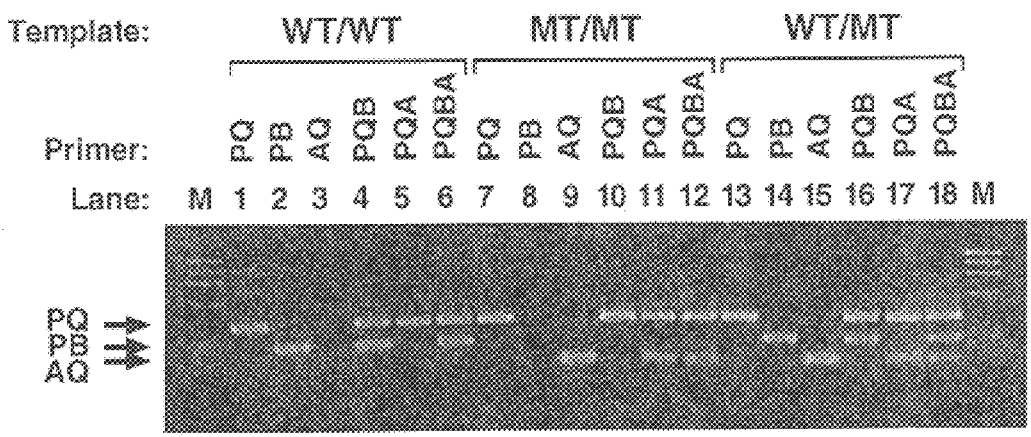

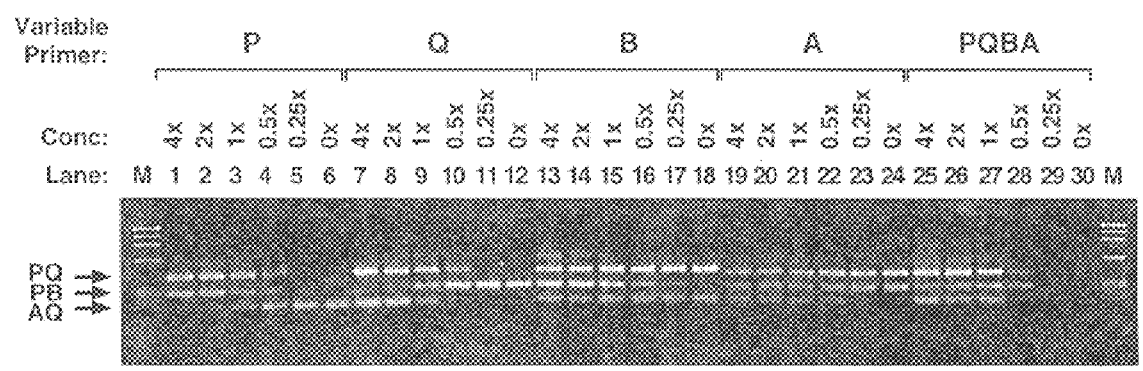

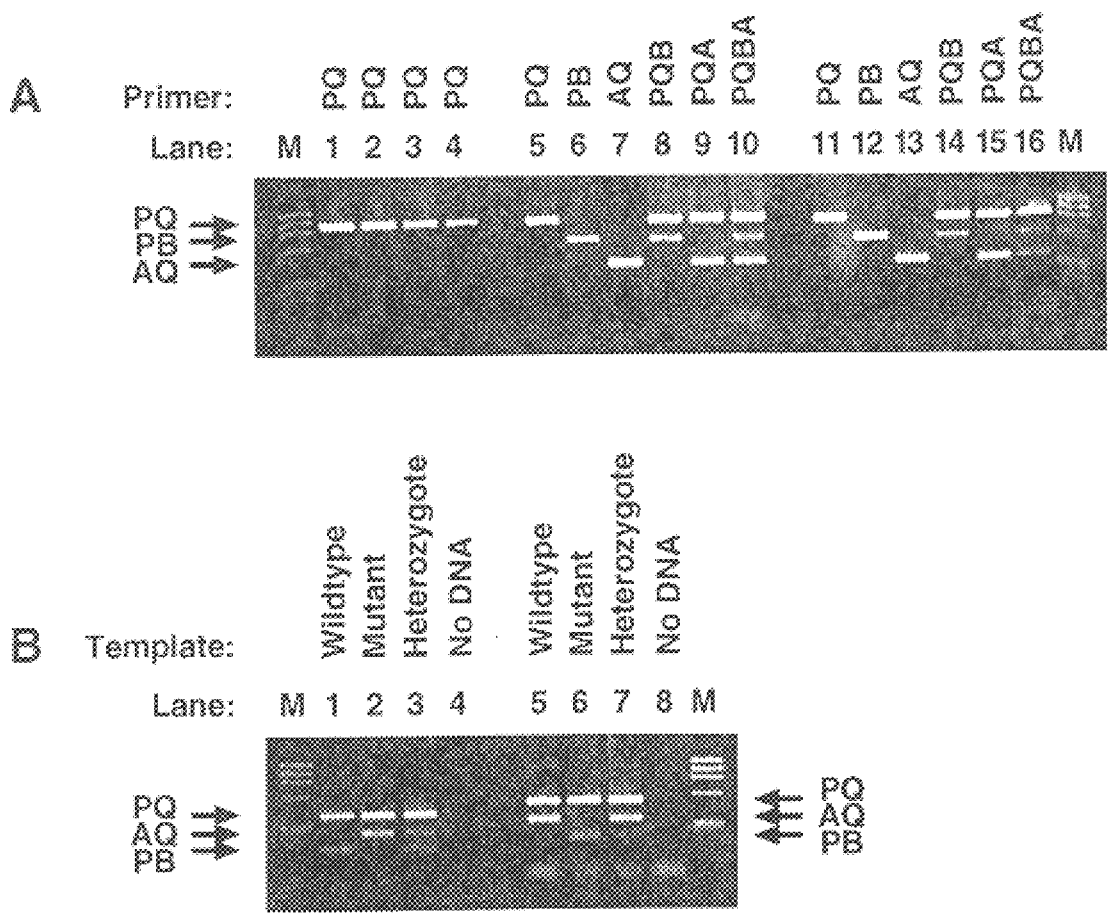

BIDIRECTIONAL PCR AMPLIFICATION OF SPECIFIC ALLELES

CROSS-REFERENCE TO RELATED APPLICATION

Benefit is claimed of provisional application Ser. No. 60/058,575, filed Sep. 11, 1997.

STATEMENT REGARDING FEDERALLY-SPONSORED RESEARCH

This invention was funded in part by the United States National Institutes of Health Grant No. MH-44276. The U.S. government may have certain rights in the invention.

BACKGROUND OF THE INVENTION

This is an invention the field of amplification of DNA by polymerase chain reaction (PCR).

PCR is a method that typically utilizes two oligonucleotide primers to amplify a DNA segment >1 million-fold. The two primers anneal to opposing strands of DNA at positions which span a target sequence of interest. A DNA polymerase is used for sequential rounds of template dependent synthesis of the DNA sequence. The PCR method is more fully described in U.S. Pat. No. 4,683,202, issued Jul. 28, 1987, the disclosure of which is incorporated herein.

PCR can be adapted for the rapid detection of single-base changes in genomic DNA by using specifically designed oligonucleotides in a method called PCR amplification of specific alleles (PASA) (Sommer et al. 1989; Sarkar et al. 1990; Wallace et al. U.S. Pat. No. 5,639,611, issued Jun. 17, 1997). This rapid method is also known as allele-specific amplification (ASA), allele-specific PCR, and amplification refractory mutation system (ARMS) (Newton et al. 1989; Nichols et al. 1989; Wu et al. 1989). For this technique an oligonucleotide primer is designed to match one allele perfectly but mismatch the other allele at or near the 3' end, thereby preferentially amplifying one allele over the other. PASA assays can be developed for assaying virtually all alleles (Sommer et al. 1992). However, each PASA reaction provides information on the presence or absence of only one allele. Two PASA reactions must be performed to determine the zygosity of any sequence change.

To detect zygosity in one PCR reaction, PCR amplification of multiple specific alleles (PAMSA) utilizes three primers in one reaction to generate two allele-specific segments that differ sufficiently in size to be distinguished by agarose gel electrophoresis (Dutton and Sommer 1991). However, problems arise from PAMSA because of differences in length, and hence, amplification efficiency of the allele-specific primers. A similar approach-termed competitive oligonucleotide primary (COP)-utilized primers that mismatched the undesired allele within the middle rather than the end of the oligonucleotide (Gibbs et al. 1989; Ruano and Kidd 1989).

Tetra-primer PCR is a method by which two allele-specific amplifications occur in opposite directions (Ye et al. 1992). Tetra-primer PCR and the method of this invention, which we have named Bi-Directional Polymerase Chain Reaction Amplification of Specific Alleles (Bi-PASA), both rely on allele-specific PCR to amplify two alleles simultaneously and in opposite directions. However, the methods differ in the following ways. (1) In tetra-primer PCR, the allele specificity of the inner primers derive from mismatches in the middle of two complementary primers, whereas, in Bi-PASA, the mismatches are at (or near) the 3' end of the primers. (2) The inner primers in Bi-PASA have short complementary segments and G+C-rich tails to efficiently switch from template-based amplification to self-amplification and to prevent megapriming. (3) Tetra-primer PCR utilizes two annealing conditions of high and low stringency, whereas Bi-PASA utilizes a constant annealing temperature. (4) The inner primers used in tetra-primer PCR are concentrated 35-fold more than the outer primers, whereas in Bi-PASA the primers are of similar concentration.

SUMMARY OF THE INVENTION

This invention is a method for conducting a bi-directional PCR amplification of specific alleles. DNA which may contain one or both of first and second alleles is subjected to a PCR utilizing an outer pair of primers P and Q and an inner pair of primers A and B.

Q is complementary to the sense strand of both alleles in a region downstream of the sequence difference (mismatch) X which distinguishes the alleles. X may be a substitution, deletion or insertion of one or more base pairs. P is complementary to the anti-sense strand of both alleles in a region upstream of X. The terms "upstream" and "downstream" relate to the direction of transcription.

B has a region at its 3' end which is complementary to the sense strand of the first allele and A has a region at its 3' end which is complementary to the antisense strand of the second allele. Each of A and B also has a non-complementary G+C-rich tail at its 5'end. X occurs at or near the 3' end of each of A and B.

DNA which is heterozygous with respect to the two alleles results in amplification of three overlapping sequences, PQ, PB and AQ. PQ, PB and AQ, respectively, stand for the sequences extending from P to Q inclusive, from P to B inclusive, and from A to Q inclusive. DNA which is homozygous with respect to the first allele results in amplification of two overlapping sequences, PQ and PB. DNA which is homozygous with respect to the second allele results in amplification of two overlapping sequences, PQ and AQ.

Following amplification, the sample can be analyzed to determine whether PB and/or AQ is present along with PQ. Preferably, the number of nucleotides separating P from X is sufficiently different from the number of nucleotides separating Q from X that the segments PB and AQ can be distinguished on an agarose gel. However, this is not necessary when other methods of analysis are used.

Bi-PASA provides a rapid, one-tube method for simultaneously differentiating homozygotes and heterozygotes. It is applicable to detecting small deletions and insertions as well as single base changes. The method is particularly useful for determining zygosity in a sample containing a wild-type allele and/or a single-base change mutant and, in general, for determining the zygosity of common sequence changes in which heterozygotes are likely to be common. By using 3 or more inner primers, it can be used to differentiate 3 or more alleles. Bi-PASA can be used to perform population screening, haplotype analysis, patient screening, and carrier testing. It is rapid, reproducible, inexpensive, non-isotopic, and amenable to automation. The method can be conducted simultaneously on 2 or more loci in different tubes, using a uniform annealing temperature.

BRIEF DESCRIPTION OF THE FIGURES

FIG. 1A is a schematic representation of Bi-PASA. The four primers (P,Q, A and B) are represented by arrows. X represents the sequence change relative to the other allele. Wavy lines on the inner primers A and B represent the non-complementary 5' tail sequences.

FIG. 1B illustrates the network structure of Bi-PASA. The four boxes represent the template used in the reaction. Arrows indicate the segments that can be produced from each template. The thickness of the arrows approximates the efficiency of amplification. The Bi-PASA reaction can be divided into two parts: template transfer amplification (genomic DNA→PQ, PB, and AQ; PQ→PB and AQ) and self-amplification (PQ→PQ, PB→PB, and AQ→AQ). The amplification efficiency, λ, for a particular segment from a given template is defined as the molecular ratio from cycle n to cycle n+1. $[PQ]_{n+1}$, $[PB]_{n+1}$ and $[AQ]_{n+1}$ are the PCR product yields of PQ, PB, and AQ, respectively, at the end of the n+1 cycle. [Genomic DNA] represents the yield of genomic DNA. The accumulation of PQ, PB, and AQ DNA products can be indicated as follows: $[PQ]_{n+1}=[PQ]_n \times (1+\lambda_n^{PQ \to PQ})+$[genomic DNA]$\times \lambda_n^{geomic\ DNA \to PQ}$; $[PB]_{n+1}+[PB]_n \times (1+\lambda_n^{PB \to PB})+\frac{1}{2} \times$[genomic DNA]$\times \lambda_n^{genomic\ DNA \to PB}+\frac{1}{2} \times [PQ] \times \lambda_n^{PQ \to PB}$; and $[AQ]_{n+1}=[AQ]_n \times (1+\lambda_n AQ \to AQ)+\frac{1}{2} \times$[genomic DNA]$\times \lambda_n^{genomic\ DNA \to AQ}+\frac{1}{2}[PQ] \times \lambda_n^{PQ \to AQ}$.

FIG. 2 illustrates the kinetics of Bi-PASA. Identical [α-32P]dATP-labeled Bi-PASA reactions were removed from the PCR thermocycler every three cycles, and the yield for each segment was quantitated with a PhosphorImager. Potentially, 135, 87 and 214 adenine nucleotides can be labeled by [α-32P]dATP in the PB, AQ and PQ segments, respectively. (FIG. 2A) All four primers were used for WT/M, WT/WT and M/M samples, indicating that the type of genomic template used can affect the yields. (FIG. 2B) The three two-primer combinations for the WT/M sample were performed. A greater yield was observed for the three segments individually as compared to the WT/M sample in FIG. 2A, indicating that interactions among the primers can influence the yield in a Bi-PASA reaction.

FIG. 3 shows the results of Bi-PASA reactions for the FV and COMT genes as described in the Examples, and illustrates interactions among the primers. Two-, three-, and four-primer combinations for the WT/WT (lanes 1–6), M/M (lanes 7–12) and WT/M (lanes 13–18) templates were amplified to observe the efficiency of the primers. (M) Size standard (120 ng of θX174/HaeIII). (FIG. 3A) COMT gene Bi-PASA reaction. The inner primers used were A2 and B3 (see Table 1 for primer specifications). The primer concentrations were 0.05 µM for P, Q and B, and 0.1 µM for A. The annealing temperature was 65° C., and 5% DMSO was added to the reaction. (FIG. 3B) FV Bi-PASA reaction. The inner primers used were A11 and B11 (see Table 1). The primer concentrations were 0.1 µM for P, B, and A, and 0.05 µM for Q. The annealing temperature was 55° C.

FIG. 4 shows the effects of primer concentrations for the FV Bi-PASA reaction. WT/M genomic DNA was used for all reactions. Lanes 1–6, 7–12, 13–18, and 19–24 show the effects of varying only the P, Q, B11 and A11 primers, respectively. Lanes 25–30 show the effects of varying all four primers at once. The primers used and the 1× concentrations were determined by the optimal conditions used in FIG. 3B. (M) Size standard (120 ng of θX174/HaeIII).

FIG. 5 shows the results of prospective study described below. Optimized BI-PASA reactions for single-base changes in the factor IX, FV-opp, and D1 genes. (M) Size standard (120 ng of φX174/HaeIII). (FIG. 5A) Optimization of the FIX gene Bi-PASA. Bi-PASA reactions shown were performed with a WT/M sample. PQ segment $T_m$=73.6° C. The annealing temperature was set at 55° C. (Lanes 1–4) PCR with each P and Q primer at 0.1, 0.05, 0.025, and 0.0125 µM concentration. Lanes 2 was designated as the minimum optimal concentration for the PQ segment. (Lanes 5–10) Control reactions with P and Q primers at 0.05 µM concentrations and A and B primers at 0.1 µM concentration. Lanes 11–16) Final Bi-PASA reaction for the FIX gene after adjustment of the A primer concentration to 0.05 µM. (FIG. 5B) Bi-PASA reaction of FV-opp and D1 genes. In the initial experiments using the FV gene, the WT and M allele-specific primers were in the upstream and downstream directions, respectively. As a test of the robustness of the Bi-PASA reaction, new primers were designed such that the WT and M allele-specific primers were in the downstream and upstream direction, respectively. WT/WT, M/M, and WT/M templates were used for optimized Bi-PASA reactions for the FV-opp and D1 genes. The $T_m$ values of the PQ segments of the FV-opp and D1 genes were 74.8° C. and 81.4° C., respectively, and the annealing temperatures were 55° C. and 60° C., respectively. Final primer concentrations for the FV-opp Bi-PASA reaction were 0.1 µM for the P primer, 0.05 µM for the Q primer, 0.1 µM for the B primer, and 0.1 µM for the A primer. Final primer concentrations for the D1 Bi-PASA reaction were 0.1 µM for the P primer, 0.1 µM for the Q primer, 0.1 µM for the B primer, and 0.1 µM for the A primer. (M) Size standard (120 ng φX171/HaeIII). (Lanes 1–4) Bi-PASA reaction for FV-opp; (lanes 5–8) bi-PASA for D1.

DETAILED DESCRIPTION OF THE INVENTION

Principle of Bi-PASA

For Bi-PASA, PCR is performed with four oligonucleotide primers: two outer primers, P and Q; and two allele-specific inner primers, A and B (FIG. 1A). Preferably, P and Q should anneal at different distances from the sequence change to differentiate the downstream AQ and upstream PB segments on an agarose gel. A and B are each specific to an allele with the mismatch at (or near, i.e, within about 3 bp of) the 3' end of the primer. A and B primers consist of two parts: a short region (about 10 to 20) that is complementary to one of the alleles and a 5' non-complementary tail. The tail sequence consists of about 6 to 20 nucleotides, preferably about 10 nucleotides, of high G+C content (about 50–100% G+C, preferably about 60 to 100%) and serves two purposes: (1) The tail acts as a "switch" from inefficient amplification of genomic DNA to efficient amplification of previously amplified template DNA; and (2) the tail prevents "megapriming", which occurs when a segment (PB or AQ) generated by PCR in an earlier cycle acts as a primer for a larger template (i.e., genomic DNA or PQ) in a subsequent cycle (Sarkar and Sommer 1990, 1992).

Depending on the zygosity, Bi-PASA produces two or three overlapping segments. PQ is always produced and serves as a positive control. PB and AQ are both present in a heterozygote (WT/M), but only PB is produced in homozygous wild-type (WT/WT) and only AQ is produced in homozygous mutant (M/M) samples.

Network Structure of Amplification Process

FIG. 1B depicts the network structure of Bi-PASA amplification for heterozygotes. Two types of amplification occur during Bi-PASA "template transfer amplification" and "self amplification." Template transfer amplification occurs when a larger template is used to produce a smaller product (genomic DNA→PQ, PB, and AQ; PQ→PB and AQ). Self-amplification occurs when a template is used to reproduce itself (PQ→PQ, PB→PB, and AQ→AQ). The amplification conditions are designed to favor self-amplification, as represented by the thickness of the arrows. The efficiency may be influenced by the cycle number and by the zygosity of the sample.

Because of the relatively short complementary region of the A and B primers that compromises efficient annealing at the annealing temperature used, the PQ template transfer amplification occurs at high efficiency compared to the efficiency of PB or AQ transfer reactions during the first few cycles of Bi-PASA. However, as the reaction progresses, PB and AQ are produced at higher efficiency because of self-amplification. Self-amplification occurs at high efficiency because both the complementary and the 10 bp tail regions are incorporated into the products providing a much longer region of complementarity.

Kinetics of Bi-PASA

To quantitate the accumulation of each segment during a Bi-PASA reaction, identical radioactive Bi-PASA reactions were removed from the thermocycler every three cycles and each segment was quantified by a PhosphorImager after agarose gel electrophoresis (FIG. 2). During cycles 18–30, PQ, PB, and AQ accumulated at remarkably similar rates, although the efficiency of accumulation for PB and AQ is somewhat greater in later cycles. In the samples from homozygous wild type or mutants (WT/WT, M/M), individual yields were up to two-fold greater in comparison to the heterozygote samples, suggesting that there are interactions among either the three segments or primers that inhibit efficiency in the WT/M sample. Thus, the type of genomic template used in the reaction may influence the efficiency of accumulation and the final amount of product produced.

For comparison, the three possible two-primer PCR amplifications were performed on the heterozygote samples. Yields of up to twofold greater were observed for each of the segments as compared to Bi-PASA with four primers. This demonstrates that interactions among primers can influence the yield in Bi-PASA.

EXEMPLIFICATION OF THE INVENTION

Methods

All primers were designed and analyzed with Oligo 4 software (National Biosciences, Inc.). Oligo 4 calculates the melting temperature values of a primer by the nearest neighbor method at 50 mM Kcl and 250 $\mu$M DNA. PCR was performed from human genomic DNA isolated from white blood cells. The PCR mixtures contained a total volume of 25 ul:50 mM Kcl, 10 mM Tris-HCl (pH 8.3), 1.5 mM MgCl2, 200 uM of each dNTP, 0.5 units ot Taq DNA polymerase (Boehringer Mannheim), and 100 ng of genomic DNA. The effects of the annealing temperature were explored extensively during the course of this study. Cycling conditions were otherwise constant. The recommended annealing temperature is 20° C. below the $T_m$ of segment PQ (see guidelines). Additional PCR cycling conditions were denaturation at 95° C. for 15 sec, annealing for 30 sec, a 1-min ramp time from the annealing temperature to the elongation temperature, and elongation at 72° C. for 2 min. An additional 15 sec of denaturation time was always supplemented during the first cycle of the reaction. Thirty cycles were performed on a Perkin Elmer GeneAmp PCR system 9600. Standard agarose gel electrophoresis with ethidium bromide staining and UV photograhy with Polaroid 667 film was used to visualize all PCR segments.

To quantitate PCR yield, PCR was performed with 5 uCi of [$\alpha$-32P]dATP per 25 $\mu$l reaction (3000 Ci/mmole, Amersham). The reaction was electrophoresed through an agarose gel, dried, and subjected to autoradiography. The PCR yield was quantitated with a PhosphorImager with ImageQuant software (Molecular Dynamics) after a 20 min exposure. The relative PCR yields were quantitated as "random units", that is, the number of pixels in the PCR band minus the background, indicated as a random unit.

Parameters Affecting Bi-PASA

The parameters important for optimizing Bi-PASA were investigated in detail for common sequence changes in the human procoagulant Factor V (FV) and catechol-O-methyltransferase (COMT) genes. A G-A transition at base pair 266 in exon 10 of the FV gene (Genbank Accession L32764 J05368) is a mutation associated with venous thromboembolism. The polymorphism in the COMT gene is a G-A transition at base pair 1947 in exon 4 (GenBank Accession Z26491). These genes were chosen partly on the basis of the large differences in G+C content (FV, 40% G+C; COMT, 63% G+C).

Table 1 lists primers designed to examine differences in mismatch position, T., of the complementary region and tail composition. In the FV gene, the position of the 3' mismatch at the −1, −2, or −3 positions did not have a noticeable effect on primer efficiency for the A primers (compare yields using A4, A6, and A7).

The $T_m$ and tail composition were both important factors in designing the inner primers. Primers in both the FV and COMT genes were much more efficient at higher $T_m$ (see Table 1 for details). The tail sequence was an important factor in primer design. Several of those with a tail of G10 were capable of priming amplification. However, primers with G9C1 or G8C2 tails were much more efficient in the Bi-PASA reactions (e.g., FV primers A8–A10 and B10 and B11).

TABLE 1

Selected Primers for the Initial
Optimazation of Fv and COMT Genes

| Name[a] | Sequence Numbers are Seq ID Nos. | WT/M | $T_m$ (° C.) | Tail | Yld[b] | [c] |
|---|---|---|---|---|---|---|
| FV gene | | | | | | |
| P  F5(25)-22D | TGCAAATGAAAACAATTTTGAA  2 | | 50.6 | | +++ | − |
| Q  F5(419)-25U | TATCACACTGGTGCTAAAAAGGACT  3 | | 53.3 | | +++ | − |
| A1  F5(257)-20D | ggggggggggTGGACAGGCA[d]  4 | A-1 M | 14.5 | G10 | − | − |
| A2  F5(256)-21D | ggggggggggCTGGACAGGCA  5 | A-1 M | 20.0 | G10 | − | − |
| A3  F5(255)-22D | ggggggggggCCTGGACAGGCA  6 | A-1 M | 29.6 | G10 | − | − |

TABLE 1-continued

Selected Primers for the Initial
Optimazation of Fv and COMT Genes

| Name[a] | Sequence Numbers are Seq ID Nos. | WT/M | $T_m$ (°C.) | Tail | Yld[b] | [c] |
|---|---|---|---|---|---|---|
| A4 FS(254)-23D | gggggggggggCCCTGGACAGGCA 7 | A-1 M | 37.4 | G10 | + | − |
| A5 FS(253)-24D | gggggggggggTCCCTGGACAGGCA 8 | A-1 M | 41.0 | G10 | + | − |
| A6 FS(255)-23D | gggggggggggCCTGGACAGGCAA 9 | A-2 M | 34.0 | G10 | + | − |
| A7 FS(256)-23D | gggggggggggCTGGACAGGCAAG 10 | A-3 M | 29.9 | G10 | + | − |
| A8 FS(254)-25D | gggggggggggCCCTGGACAGGCAAG 11 | A-3 M | 43.3 | G10 | + | − |
| A9 FS(254)-23D | ggggcggggCCCTGGACAGGCA 12 | A-1 M | 37.4 | G9C1 | ++ | − |
| A10 FS(254)-23D | gcgggcggggCCCTGGACAGGCA 13 | A-1 M | 37.4 | G8C2 | +++ | − |
| A11 FS(253)-24D | gcgggcggggTCCCTGGACAGGCA 14 | A-1 M | 41.0 | G8C2 | +++ | − |
| B1 F5(276)-20U | gggggggggggTGTATTCCTC 15 | C-1 WT | −3.8 | G10 | − | − |
| B2 FS(277)-21U | gggggggggggCTGTATTCCTC 16 | C-7 WT | 3.3 | G10 | − | − |
| B3 FS(278)-22U | gggggggggggCCTGTATTCCTC 17 | C-1 WT | 14.5 | G10 | − | − |
| B4 FS(279)-23U | gggggggggggACCTGTATTCCTC 18 | C-1 WT | 18.4 | G10 | − | − |
| BS FS(280)-24U | gggggggggggTACCTGTATTCCTC 19 | C-1 WT | 20.7 | G10 | − | − |
| B6 FS(282)-26U | gggggggggggAATACCTGTATTCCTC 20 | C-1 WT | 28.0 | G10 | − | − |
| B7 FS(284)-28U | gggggggggggAAAATACCTGTATTCCTC 21 | C-1 WT | 34.7 | G10 | − | − |
| B8 FS(278)-24U | gggggggggggCCTGTATTCCTCGC 22 | C-3 WT | 33.2 | G10 | − | − |
| B9 FS(279)-25U | gggggggggggGACCTGTATTCCTCGC 23 | C-3 WT | 35.6 | G10 | − | − |
| B10 FS(280)-26U | gggggggggggTACCTGTATTCCTCGC 24 | C-3 WT | 36.7 | G10 | + | − |
| B11 FS(280)-26U | ggggcggggcgTACCTGTATTCCTCGC 25 | C-3 WT | 36.7 | G8C2 | +++ | − |
| B12 FS(284)-28U | ggggcggggcgAAAATACCTGTATTCCTC 26 | C-1 WT | 34.7 | G8C2 | +++ | − |
| COMT gene | | | | | | |
| P CDMT(1706)-25D | ATCCAAGTTCCCCTCTCTCCACCTG 27 | | 61.6 | | +++ | − |
| Q CGMT(2511)-25U | GTTGGGGCTCACCTCCAAGAGAAGC 28 | | 66.7 | | +++ | − |
| A1 COMT(1934)-24D | ggggcggggcGGATTTCGCTGGCA 29 | A-1 M | 41.7 | G8C2 | +/− | − |
| A2 CDMT(1932)-26D | ggggcggggcGTGGATTTCGCTGGCA 3C | A-1 M | 47.5 | G8C2 | +++ | − |
| A3 CDMT(193D)-28D | ggggcggggcTGGTGGATTTCGCTGGCA 31 | A-1 M | 55.6 | G8C2 | +++ | − |
| A4 CCMT(1928)-3QD | ggggcggggcGATGGTGGATTTCGCTGGCA 32 | A-1 M | 58.1 | G8C2 | +++ | − |
| B1 CDMT(1960)-24U | ggggcggggcgACCTTGTCCTTCAC 33 | C-1 WT | 27.C | G8C2 | − | − |
| B2 COMT(1962)-26U | ggggcggggcgACACCTTGTCCTTCAC 34 | C-1 WT | 34.7 | G8C2 | +/− | − |
| E3 CCMT(1964)-28U | ggggcggggcgGCACACCTTGTCCTTCAC 35 | C-1 WT | 45.0 | G8C2 | +++ | − |
| B4 CDMT(1966)-3DU | ggggcggggcgATGCACACCTTGTCCTTCAC 36 | C-1 WT | 49.6 | G8C2 | +++ | + |
| B5 CCMT(1968)-32U | ggggcggggcgGCATGCACACCTTGTCCTTCAC 37 | C-1 WT | 56.8 | G8C2 | +++ | + |

[a]The sequence of the FV gene was from a revised version of GenBank Accession L32764 J05368 with an additional 127 base sequence in intron 10, as shown in Seq. ID 1. As an example for oligo-nucleotide P, F5 = FV, (25) − 22D = 5' end of the primer beginning at 25 (numbering as shown above), and the length is 22 bases downstream (D) (i.e., in the direction of transcription). The precise sizes and locations of the PCR fragment can be obtained from the informative names. The#
sequence of the COMT gene was from a revised version of GenBank Accession Z26491, in which a 122 base sequence was inserted after base 2084, as shown in Seq ID 48.

TABLE 1-continued

Selected Primers for the Initial
Optimazation of Fv and COMT Genes

| Name[a] | Sequence Numbers are Seq ID Nos. | WT/M | $T_m$ (° C.) | Tail | Yld[b] | [c] |
|---|---|---|---|---|---|---|

[b]under optimal PCR conditions, the relative yield of the DNA products as indicated as -, no DNA band(s) on the agarose gel stained by ethidium bromide for UV photograph; +/\, very weak DNA bankd; I, weak DNA band; ++, strong DNA band; +++, very strong DNA band.
[c]specificity - defined as amplification of only the expected allele. (-) No mismatched amplified PCR DNA with homozygote wild-type and mutant genomic DNA template; (+) false-amplified PCR DNA.
[d]The lowercase letters indicate noncomplementary and the uppercase letters indicate complementary sequences. Also the nucleotide at the mutation site is in boldface type.
[e](A-1M) the first base from the 3' end is a mutated A nucleotide.

Seq. ID 1: Exon 10 of FV gene (bases 1–319) and 127 base intron sequence (bases 320–446 shown in lower case)
1 TTATTTATTA TCATGAAATA ACTTTGCAAA TGAAAACAAT TTTGAATATA
51 TTTTCTTTCA GGCAGGAACA ACACCATGAT AGTTTGATGA ACCCACAGAA
101 AAACCTATAC TTATAAGTGG AACATCTTAG AGTTTGATGA ACCCACAGAA
151 AATGATGCCC AGTGCTTAAC AAGACCATAC TACAGTGACG TGGACATCAT
201 GAGAGACATC GCCTCTGGGC TAATAGGACT ACTTCTAATC TGTAAGAGCA
251 GATCCCTGGA CAGGCGAGGA ATACAGGTAT TTTGTCCTTG AAGTAACCTT
301 TCAGAAATTC TGAGAATTTC ttctggctag aacatgttag gtctcctggc
351 taaataatgg ggcatttcct tcaagagaac agtaattgtc aagtagtcct
401 ttttagcacc agtgtgataa catttattct ttttttttt ttgtct
Seq. ID 48: Bases 1701–2520 of COMT gene, a revised version of Genbank Accession Z26491 in which a 122 base region in intron 4 (bases 2085–2206, shown in lower case) is inserted.
1701 TGGGGATCCA AGTTCCCCTC TCTCCACCTG TGCTCACCTC TCCTCCGTCC
1751 CCAACCCTGC ACAGGCAAGA TCGTGGACGC CGTGATTCAG GAGCACCAGC
1801 CCTCCGTGCT GCTGGAGCTG GGGGCCTACT GTGGCTACTC AGCTGTGCGC
1851 ATGGCCCGCC TGCTGTCACC AGGGGCGAGG CTCATCACCA TCGAGATCAA
1901 CCCCGACTGT GCCGCCATCA CCCAGCGGAT GGTGGATTTC GCTGGCGTGA
2001 GCTGTGGGCA GGGCGGGCAT GCGCACTTTG ATCCTCCCCA CCAGGTGTTC
2051 ACACCACGTT CACTGAAAAC CCACTATCAC CAGGccccctc agtgcttccc
2101 agcctggggc tgaggaaaga ccccccccagc agctcagtga gggtctcaca
2151 gctctgggta aactgccaag gtggcaccag gaggggcagg gacagagtgg
2201 ggccttGTCA TCCCAGAACC CTAAAGAAAA CTGATGAATG CTTGTATGGG
2251 TGTGTAAAGA TGGCCTCCTG TCTGTGTGGG CGTGGGCACT GACAGGCGCT
2301 GTTGTATAGG TGTGTAGGGA TGGCCTCCTG TCTGTGAGGA CGTGGGCACT
2351 GACAGGCGCT GTTCCAGGTC ACCCTTGTGG TTGGAGCGTC CCAGGACATC
2401 ATCCCCCAGC TGAAGAAGAA GTATGATGTG GACACACTGG ACATGGTCTT
2451 CCTCGACCAC TGGAAGGACC GGTACCTGCC GGACACGCTT CTCTTGGAGG
2501 TGAGCCCCAA CCAGGATGGC Interactions Among Primers FIG. 3 illustrates Bi-PASA reactions for the COMT and FV genes. Various combinations of the primers listed in Table 1 were used to identify the optimal set of inner primers and reaction conditions for these genes (the optimal primers and conditions can be found in the legend to FIG. 3). To visualize the interactions among the primers in Bi-PASA, reactions were performed with different sets of the four optimal primers on the three genomic templates. FIG. 3A shows the Bi-PASA reaction for the COMT gene. Interactions among the primers affect both the yield and the specificity of the reactions. In general, the greater the number of primers added to the reaction, the lower the yield is of the individual segments (cf. lanes 2, 4, and 6). The specificity of the inner primers to a particular allele can also be affected because of the competition between the primers. Lane 8 shows a faint false-positive signal for the nonspecific allele for the two-primer combination. However, the non-specificity disappears when more primers are added to the reaction as in lanes 10 and 12. FIG. 3B shows the Bi-PASA reaction for the FV gene. Specificity was not a problem, but again the yield was affected by the number of primers in the reaction.

Primer concentrations were optimized for the COMT and FV Bi-PASA reactions. The outer and inner primer concentrations were adjusted to the minimum optimal point at which the wild-type and mutant alleles could be amplified specifically and efficiently (see FIG. 3). FIG. 4 shows the effects on the FV Bi-PASA reaction when the concentrations of each individual primer and then all four primers were varied. A change in the concentration of a primer can affect all of the segments produced in the reaction, for example, FIG. 4, lanes 1–6, demonstrates that when the concentratin of the P primer is varied, not only do the yields of the PQ and PB segments vary (which would be expected) but the AQ segment is also affected. This demonstrates again that interactions among the primers are an important factor in a Bi-PASA reaction.

Blinded Analysis

To test the sensitivity and specificity of Bi-PASA under actual screening conditions, a blinded analysis of the COMT gene was performed. For the common COMT polymorphism, 249 samples were screened independently by RFLP analysis and Bi-PASA. The sensitivity and specificity were 100% and 99.6%, respectively; the one false-positive result was attributable to contamination by the neighboring well of a gel.

The sensitivity of Bi-PASA was also tested by diluting the mutant allele into the wild-type allele. Detection of the mutant allele by staining with ethidium bromide was possible with a 20- to 40-fold excess of the wild-type allele (data not shown).

Guidelines for Primer Design

Reactions were designed successfully to detect sequence changes in the FV and COMT genes. For Bi-PASA to be a useful tool, optimization needs to be relatively rapid and simple. On the basis of experience gained by analysis of multiple primers and optimization parameters, guidelines for primer design and a strategy for reaction optimization were developed. Although subsequent experiments support the utility of the guidelines and strategy, the folowing guidelines will liekly evolve with time. Desiging the primers is a critical step in successful Bi-PASA reaction. The $T_m$ value of each PCR segment was estimated by the formula of Wetmur (1991): $T_m^{product}=81.5+16.6\ log[K^+]+0.41(\%G+\%C)-675/length$.

1. The $T_m$ value of P and Q (outer primers) should be 20–25° C. lower than that of the PQ segment. A good size for the PQ segment is about 300–1000 bp, although the method can be used with much longer PQ segments. For the COMT gene, the $T_m$ value of the PQ PCR product was 83.8° C. For the FV gene, the $T_m$ value of the PQ PCR product was 74.8° C. The $T_m$ value of successful P and Q primers were 61.6° C. and 66.7° C. for COMT gene, and 50.6° C. and 53.3° C. for FV gene, respectively. When P and Q were designed with a lower $T_m$ value, the interactions among the four primers were more pronounced, especially for regions of high G+C content (data not shown).

2. The $T_m$ values of the complementary region of inner primers A and B should be −35° C. lower than that of the PQ segment. Parameters were optimized in the COMT and FV genes by systematically increasing the length of the complementary regions of the inner primers. It was observed that once the $T_m$ value of the inner primers reached a certain point below the $T_m$ of the PQ PCR products, the inner primers began to work with high yield and specificity (see Table 1). For the COMT gene, this "'threshold" $T_m$ value was 47.5° C. in A2 and 45.0° C. in B3, which were 36.3° C. and 38.8° C. below the $T_m$ value of the PQ PCR DNA product, respectively. Beyond that point, $T_m$ was 55.6° C. in A3, 58.1° C. in A4, 49.6° C. in B4, and 56.8° C. in B5, all having produced high-yield AQ and BP segments, respectively. However, B4 and B5 also amplified a faint false-positive segment when M/M genomic DNA was used, indicating that as primer length increases, some specificity may be sacrificed. In the FV gene, the threshold $T_m$ was 37.4° C. for A4 and 34.7° C. for B7, which is 37.4° C. and 40.1° C. below the $T_m$ of the PQ segment, respectively. The A and B inner primers were $T_m$ values above this point also amplified with high yield and specificity (see Table 1).

3. The annealing temperature should be 20° C. below the $T_m$ value of the PQ segment in these studies. The optimal annealing temperature also was closely linked to the $T_m$ value of the PQ PCR products. The annealing temperature was set relatively high to avoid hybridization among the multiple PCR segments. For the analyzed regions, the recommended annealing temperatures happen to be within 2° C. of the annealing temperatures estimated by the formula of Rychlik et al. (1990), $T_m^{annealing}=0.3\times T_m^{P\ or\ Q\ primer}+0.7\times T_m^{PQ\ product}-14.9$.

In the COMT gene, good results could be achieved only within a narrow range of annealing temperatures. When the annealing temperature was set at 55° C. or 60° C., the yield and specificity were poor in comparison to the recommended temperature of 65° C. However, good results were achieved for the FV gene with annealing temperatures ranging from 50° C.–60° C. (data not shown).

Strategy of Optimization of Bi-PASA

1. Design the primers based on the above guidelines.

2. Alter the concentration of P and Q. This seems to have more effect on the yields of all the segments than altering the concentration of the inner primers A and B. Optimize the PQ segment by titrating oligonucleotide concentrations. Use the lowest concentration of primer. necessary to obtain a high yield. For regions of high G+C content, DMSO may be used.

3. Determine the range of oligonucleotide concentrations with robust specification that are compatible with primers P and B and perform a similar analysis with primers A and Q. Then adjust the concentrations of the inner primers such that appropriate amplifications with three primers (PQB and PQA) or four primers (PQBA) occur (see FIGS. 3 and 5). If it is not possible to achieve acceptable yield but the specificity is good, increase the length of the complementary regions of the inner primers and reoptimize. If specificity is not optimal, decrease the length of the inner primers or alter the position of the mismatch by 1 bp or more. This should be performed for WT/WT, WT/M, and M/M samples.

4. Once the above conditions have been satisifed, check the sensitivity and specificity of the reaction. Dilute the DNA samples to determine the minimum amount of template necessary to perform the reaction. Dilute the M sample into the WT sample and vice versa to determine the maximum ratio of WT to M that can be detected.

Prospective Test of the Guidelines and Strategy

To test the utility of the guidelines and strategy, three Bi-PASA reactions were designed (Table 2) and tested for (1) the TaqI polymorphism in the factor IX gene, (2) the FV Leiden mutation assayed in a direction opposite to that performed initially, and (3) a polymorphism in the D1 dopamine receptor genes, respectively. All the reactions were successful and rapidly optimized by utilizing the above primer guidelines and optimization strategy (FIG. 5).

TABLE 2

List of Primers in the Prospective Study

| Name[a] | Sequence Numbers are Seq. ID Nos. | WT/M | $T_m$(° C.) | Tail | Yield[b] | Specificity[c] |
|---|---|---|---|---|---|---|
| FIX[a] | | | | | | |
| P F9(10545)-24D | TCCCTCTGAAACAAGTTGAAACTG 38 | | 54.3 | | +++ | − |
| Q E9(11446)-23U | TCATCTGTCAGGTGGATTGCTGT 39 | | 55.9 | | +++ | − |
| A F9(11095)-30D | ggggcggggcTGACTATATTGATTACATCG 40 | G-1 WT | 37.3 | G8C2 | +++ | − |

TABLE 2-continued

List of Primers in the Prospective Study

| Name[a] | Sequence Numbers are Seq. ID Nos. | WT/M | $T_m$(° C.) | Tail | Yield[b] | Specificity[c] |
|---|---|---|---|---|---|---|
| B E9(11129)-28U | ggggcgggcgGCTATGTAACATTTTTGA 41 | T-3 M | 34.8 | G8C2 | +++ | − |
| FV(opp)[c]: | Numbers are Seq. ID Nos. | | | | | |
| A F5(254)-23D | gcgggcggggCCCTGGACAGGCC 42 | C-1 WT | 37.4 | G8C2 | +++ | − |
| B F5(280)-26U | ggggcgggcgTACCTGTATTCCTTGC 43 | C-3 M | 33.5 | G8C2 | +++ | − |
| D1[d]: | | | | | | |
| P D1(33)-24D | GACCTGCAGCAAGGGAGTCAGAAG 44 | | 60.3 | | +++ | − |
| Q D1(544 )-24U | AGAAGCCAGCAATCTCAGCCACTG 45 | | 60.7 | | +++ | − |
| A D1(213)-27D | ggggcgcgtCCCCTATTCCCTGCTTG 46 | G-1 M | 47.5 | G6C3T1 | +++ | − |
| B D1(299)-28U | ggggcgggCgGACACCCCTCAAGTTCCT 47 | T-1 WT | 45.4 | G8C2 | +++ | − |

[a]See Table 1 footnote for details on primer sequence, etc.
[b]The sequence of the FIX gene was numbered on the basis of Yoshitake et al. (1985).
[c]The P and Q primers for FV (opp) were the same as used in FV (see Table 1).
[d]The sequence of the D1 gene was submitted to GenBank under accession no. X55760.Gb_Pr.

REFERENCES

Dutton, C. And S. S. Sommer. 1991. Simultaneous detection of multiple single-base alleles at a polymorphic site. *BioTechniques* 11:700–702

Gibbs, R. A., P. Nguyen, and C. T. Caskey. 1989. Detection of single DNA base differences by competitive oligonucleotide priming. *Nucleic Acids Res.* 17:2437–2448.

Newton, C. R., A. Graham, L. E. Heptinstall, S. J. Powell, C. Summers, N. Kalsheker, J. G. Smith, and A. F. Markham. 1989. Analysis of any point mutation in DNA. The amplification refractory mutation system (ARMS). *Nucleic Acids Res.* 17:2503–2516.

Nichols, W. C., J. J. Liepnieks, V. A. McKusick, and M. D. Benson. 1989. Direct sequencing of the gene for Maryland/German familial amyloidotic polyneuropathy type II and genotyping by allele-specific enzymatic amplification. *Genomics* 5:535–540.

Ruano, G. and K. K. Kidd. 1989. Direct haplotyping of chromosomal segments from multiple heterozygotes via allele-specific PCR amplification. *Nucleic Acids Res.* 17:8392.

Rychlik, W., W. J. Spencer, and R. E. Rhoads. 1990. Optimization of the annealing temperature of DNA amplification in vitro. *Nucleic Acids Res.* 18:6409–6412.

Sarkar, G. and S. S. Sommer. 1990. The "megaprimer" method of site-directed mutagenesis. *BioTechniques* 8:404–407.

Sarkar, G and S. S. Sommer 1992. Double-standard DNA segments can efficiently prime the amplification of human genomic DNA. *Nucleic Acids Res.* 20:4937–4938.

Sarkar, G., J. Cassady, C. D. K. Bottema, and S. S. Sommer. 1990. Characterization of polymerase chain reaction amplification of specific alleles. *Anal. Biochem.* 186:64–68.

Sommer, S. S., J. D. Cassady, J. L. Sobell, and C. D. K. Bottema. 1989. A novel method for detecting point mutations or polymorphisms and its application to population screening for carriers of phenylketonuria. *Mayo Clin. Proc.* 64:1361–1372.

Sommer, S. S. A. R. Groszbach, and C. D. K. Bottema. 1992. PCR amplification of specific alleles (PASA) is a general method for rapidly detecting known single-base changes. *BioTechniques* 12:82–87.

Wetmur, J. G. 1991. DNA Probes: Application of the principles of nucleic acid hybridization. *Crit. Rev. Biochem. Mol. Biol.* 26:227–259.

Wu, D. Y., L. Ugozzoli, B. K. Pal, and R. B. Wallace. 1989. Allele-specific enzymatic amplification of β-globin genomic DNA for diagnosis of sickle cell anemia. *Proc. Natl. Acid. Sci.* 86:2757–2760.

Ye, S., S. Humphries, and F. Green. 1992. Allele specific amplification by tetra-primer PCR. *Nucleic Acids Res.* 20:1152.

Yositake, S., B. G. Schach, D. C. Foster, E. W. Davie, and K. Kuarchi. 1985. Nucleotide sequence of the gene for human factor IX (anti-hemophiliac factor B). *Biochemistry* 24:3736–3750.

What is claimed is:

1. A method for conducting a bi-directional PCR amplification of specific alleles which comprises subjecting DNA which may contain one or both of first and second alleles to a single one tube PCR under a thermal cycling condition utilizing an outer pair of primers P and Q and an inner pair of primers A and B, where Q is complementary to the sense strand of both alleles in a region downstream of the sequence difference X which distinguishes the alleles and P is complementary to the anti-sense strand of both alleles in a region upstream of X;

B has a region at its 3' end which is complementary to the sense strand of the first allele and A has a region at its 3' end which is complementary to the antisense strand of the second allele, each of A and B also has a non-complementary G+C-rich tail at its 5' end, and X occurs at or near the 3' end of each of A and B, whereby A and B are in two directions with partially overlapped 3' ends;

whereby DNA which is heterozygous with respect to the two alleles results in simultaneous amplification of three overlapping sequences, PQ, PB and AQ, DNA which is homozygous with respect to the first allele results in simultaneous amplification of two overlapping sequences, PQ and PB, and DNA which is homozygous with respect to the second allele results in simultaneous amplification of two overlapping sequences, PQ and AQ, where PQ, PB and AQ, respectively, stand for the sequences extending from P to Q inclusive, from P to B inclusive, and from A to Q inclusive, wherein the method is conducted at a substantially constant annealing temperature in the range of about 50–65° C. and with a ratio of concentrations of the outer and inner primers in the PCR mixture in the range of about 1:1 to 1:6.

2. Method of claim 1 wherein X is a base substitution, deletion or insertion.

3. Method of claim 2 wherein the the complementary regions of both primers A and B are about 10 to 20 nucleotides in length, the G+C-rich tails of both primers A and B are about 6 to 20 nucleotides in length, and the G+C-rich tails contain about 50 to 100% G+C.

4. A method for conducting a bi-directional PCR amplification of specific alleles in DNA which may contain one or both of first and second alleles, one of which is a mutant allele containing a point mutation X and one of which is a wild type allele, which comprises subjecting the DNA to a single one-tube PCR under a thermal cycling condition utilizing an outer pair of primers P and Q and an inner pair of primers A and B, where Q is complementary to the sense strand of both alleles in a region downstream of X and P is complementary to the anti-sense strand of both alleles in a region upstream of X;

B has a region at its 3' end which is complementary to the sense strand of the first allele and A has a region at its 3' end which is complementary to the antisense strand of the second allele, each of A and B also has a non-complementary G+C-rich tail at its 5' end, and X occurs at or near the 3' end of each of A and B, whereby A and B are in two directions with partially overlapped 3' ends;

whereby DNA which is heterozygous with respect to the two alleles results in simultaneous amplification of three overlapping segments, PQ, PB and AQ, DNA which is homozygous with respect to the first allele results in simultaneous amplification of two overlapping segments, PQ and PB, and DNA which is homozygous with respect to the second allele results in simultaneous amplification of two overlapping segments, PQ and AQ, where PQ, PB and AQ, respectively, stand for the segments extending from P to Q inclusive, from P to B inclusive, and from A to Q inclusive, wherein the method is conducted at a substantially constant annealing temperature in the range of about 50–65° C. and with a ratio of concentrations of the outer and inner primers in the PCR mixture in the range of about 1:1 to 1:6.

5. Method of claim 4 wherein the annealing temperature is about 20–25° C. below the Tm of the segment PQ.

6. Method of claim 5 wherein the Tm values of outer primers P and Q are about 20–25° C. lower than that of the PQ segment.

7. Method of claim 6 wherein the Tm values of the complementary regions of the inner primers A and B are about 35° C. lower than that of the PQ segment.

8. Method of claim 1 wherein 3 or more inner primers are used to differentiate 3 or more alleles.

9. Method of claim 8 wherein 3 or more inner primers are used to differentiate 3 or more alleles.

10. Method of claim 1 wherein a uniform annealing temperature is used to conduct the method on 2 or more loci.

11. Method of claim 8 wherein a uniform annealing temperature is used to conduct the method on 2 or more loci.

12. Method of claim 1 wherein B and A primers have the same or different 5' tails.

13. Method of claim 1 wherein the tail of primer B or A forms a stem-loop structure within its sequence.

* * * * *

SEQUENCE LISTING

<160> NUMBER OF SEQ ID NOS: 48

<210> SEQ ID NO 1
<211> LENGTH: 446
<212> TYPE: DNA
<213> ORGANISM: Homo sapiens
<220> FEATURE:

-continued

<400> SEQUENCE: 1

| ttatttatta tcatgaaata actttgcaaa tgaaaacaat tttgaatata ttttctttca | 60 |
| ggcaggaaca acaccatgat agtttgatga acccacagaa aaacctatac ttataagtgg | 120 |
| aacatcttag agtttgatga acccacagaa aatgatgccc agtgcttaac aagaccatac | 180 |
| tacagtgacg tggacatcat gagagacatc gcctctgggc taataggact acttctaatc | 240 |
| tgtaagagca gatccctgga caggcgagga atacaggtat tttgtccttg aagtaacctt | 300 |
| tcagaaattc tgagaatttc ttctggctag aacatgttag gtctcctggc taaataatgg | 360 |
| ggcatttcct tcaagagaac agtaattgtc aagtagtcct ttttagcacc agtgtgataa | 420 |
| catttattct tttttttttt ttgtct | 446 |

<210> SEQ ID NO 2
<211> LENGTH: 22
<212> TYPE: DNA
<213> ORGANISM: Homo sapiens

<400> SEQUENCE: 2

| tgcaaatgaa aacaattttg aa | 22 |

<210> SEQ ID NO 3
<211> LENGTH: 25
<212> TYPE: DNA
<213> ORGANISM: Homo sapiens

<400> SEQUENCE: 3

| tatcacactg gtgctaaaaa ggact | 25 |

<210> SEQ ID NO 4
<211> LENGTH: 20
<212> TYPE: DNA
<213> ORGANISM: Homo sapiens

<400> SEQUENCE: 4

| gggggggggg tggacaggca | 20 |

<210> SEQ ID NO 5
<211> LENGTH: 21
<212> TYPE: DNA
<213> ORGANISM: Homo sapiens

<400> SEQUENCE: 5

| gggggggggg ctggacaggc a | 21 |

<210> SEQ ID NO 6
<211> LENGTH: 22
<212> TYPE: DNA
<213> ORGANISM: Homo sapiens

<400> SEQUENCE: 6

| gggggggggg cctggacagg ca | 22 |

<210> SEQ ID NO 7
<211> LENGTH: 23
<212> TYPE: DNA
<213> ORGANISM: Homo sapiens

<400> SEQUENCE: 7

| gggggggggg ccctggacag gca | 23 |

<210> SEQ ID NO 8
<211> LENGTH: 24
<212> TYPE: DNA
<213> ORGANISM: Homo sapiens

<400> SEQUENCE: 8
gggggggggg tccctggaca ggca                                              24

<210> SEQ ID NO 9
<211> LENGTH: 23
<212> TYPE: DNA
<213> ORGANISM: Homo sapiens

<400> SEQUENCE: 9
gggggggggg cctggacagg caa                                               23

<210> SEQ ID NO 10
<211> LENGTH: 23
<212> TYPE: DNA
<213> ORGANISM: Homo sapiens

<400> SEQUENCE: 10
gggggggggg ctggacaggc aag                                               23

<210> SEQ ID NO 11
<211> LENGTH: 25
<212> TYPE: DNA
<213> ORGANISM: Homo sapiens

<400> SEQUENCE: 11
gggggggggg ccctggacag gcaag                                             25

<210> SEQ ID NO 12
<211> LENGTH: 23
<212> TYPE: DNA
<213> ORGANISM: Homo sapiens

<400> SEQUENCE: 12
gggggcgggg ccctggacag gca                                               23

<210> SEQ ID NO 13
<211> LENGTH: 23
<212> TYPE: DNA
<213> ORGANISM: Homo sapiens

<400> SEQUENCE: 13
gcgggcgggg ccctggacag gca                                               23

<210> SEQ ID NO 14
<211> LENGTH: 24
<212> TYPE: DNA
<213> ORGANISM: Homo sapiens

<400> SEQUENCE: 14
gcgggcgggg tccctggaca ggca                                              24

<210> SEQ ID NO 15
<211> LENGTH: 20
<212> TYPE: DNA
<213> ORGANISM: Homo sapiens

<400> SEQUENCE: 15
gggggggggg tgtattcctc                                                   20

<210> SEQ ID NO 16
<211> LENGTH: 21
<212> TYPE: DNA
<213> ORGANISM: Homo sapiens

<400> SEQUENCE: 16
gggggggggg ctgtattcct c                                    21

<210> SEQ ID NO 17
<211> LENGTH: 22
<212> TYPE: DNA
<213> ORGANISM: Homo sapiens

<400> SEQUENCE: 17
gggggggggg cctgtattcc tc                                   22

<210> SEQ ID NO 18
<211> LENGTH: 23
<212> TYPE: DNA
<213> ORGANISM: Homo sapiens

<400> SEQUENCE: 18
gggggggggg acctgtattc ctc                                  23

<210> SEQ ID NO 19
<211> LENGTH: 24
<212> TYPE: DNA
<213> ORGANISM: Homo sapiens

<400> SEQUENCE: 19
gggggggggg tacctgtatt cctc                                 24

<210> SEQ ID NO 20
<211> LENGTH: 26
<212> TYPE: DNA
<213> ORGANISM: Homo sapiens

<400> SEQUENCE: 20
gggggggggg aatacctgta ttcctc                               26

<210> SEQ ID NO 21
<211> LENGTH: 28
<212> TYPE: DNA
<213> ORGANISM: Homo sapiens

<400> SEQUENCE: 21
gggggggggg aaaatacctg tattcctc                             28

<210> SEQ ID NO 22
<211> LENGTH: 24
<212> TYPE: DNA
<213> ORGANISM: Homo sapiens

<400> SEQUENCE: 22
gggggggggg cctgtattcc tcgc                                 24

<210> SEQ ID NO 23
<211> LENGTH: 25
<212> TYPE: DNA
<213> ORGANISM: Homo sapiens

<400> SEQUENCE: 23

```
gggggggggg acctgtattc ctcgc                                           25
```

<210> SEQ ID NO 24
<211> LENGTH: 26
<212> TYPE: DNA
<213> ORGANISM: Homo sapiens

<400> SEQUENCE: 24

```
gggggggggg tacctgtatt cctcgc                                          26
```

<210> SEQ ID NO 25
<211> LENGTH: 25
<212> TYPE: DNA
<213> ORGANISM: Homo sapiens

<400> SEQUENCE: 25

```
ggggcgggcg taccgtattc ctcgc                                           25
```

<210> SEQ ID NO 26
<211> LENGTH: 28
<212> TYPE: DNA
<213> ORGANISM: Homo sapiens

<400> SEQUENCE: 26

```
ggggcgggcg aaaatacctt gattcctc                                        28
```

<210> SEQ ID NO 27
<211> LENGTH: 25
<212> TYPE: DNA
<213> ORGANISM: Homo sapiens

<400> SEQUENCE: 27

```
atccaagttc ccctctctcc acctg                                           25
```

<210> SEQ ID NO 28
<211> LENGTH: 25
<212> TYPE: DNA
<213> ORGANISM: Homo sapiens

<400> SEQUENCE: 28

```
gttggggctc acctccaaga gaagc                                           25
```

<210> SEQ ID NO 29
<211> LENGTH: 24
<212> TYPE: DNA
<213> ORGANISM: Homo sapiens

<400> SEQUENCE: 29

```
ggggcgggc ggatttcgct ggca                                             24
```

<210> SEQ ID NO 30
<211> LENGTH: 26
<212> TYPE: DNA
<213> ORGANISM: Homo sapiens

<400> SEQUENCE: 30

```
ggggcgggc gtggatttcg ctggca                                           26
```

<210> SEQ ID NO 31
<211> LENGTH: 28
<212> TYPE: DNA
<213> ORGANISM: Homo sapiens

<400> SEQUENCE: 31

-continued ggggcggggc tggtggattt cgctggca                                          28

<210> SEQ ID NO 32
<211> LENGTH: 30
<212> TYPE: DNA
<213> ORGANISM: Homo sapiens

<400> SEQUENCE: 32
ggggcggggc gatggtggat tcgctggca                                         30

<210> SEQ ID NO 33
<211> LENGTH: 24
<212> TYPE: DNA
<213> ORGANISM: Homo sapiens

<400> SEQUENCE: 33
ggggcgggcg accttgtcct tcac                                              24

<210> SEQ ID NO 34
<211> LENGTH: 26
<212> TYPE: DNA
<213> ORGANISM: Homo sapiens

<400> SEQUENCE: 34
ggggcgggcg acaccttgtc cttcac                                            26

<210> SEQ ID NO 35
<211> LENGTH: 28
<212> TYPE: DNA
<213> ORGANISM: Homo sapiens

<400> SEQUENCE: 35
ggggcgggcg gcacaccttg tccttcac                                          28

<210> SEQ ID NO 36
<211> LENGTH: 30
<212> TYPE: DNA
<213> ORGANISM: Homo sapiens

<400> SEQUENCE: 36
ggggcgggcg atgcacacct tgtccttcac                                        30

<210> SEQ ID NO 37
<211> LENGTH: 32
<212> TYPE: DNA
<213> ORGANISM: Homo sapiens

<400> SEQUENCE: 37
ggggcgggcg gcatgcacac cttgtccttc ac                                     32

<210> SEQ ID NO 38
<211> LENGTH: 24
<212> TYPE: DNA
<213> ORGANISM: Homo sapiens

<400> SEQUENCE: 38
tccctctgaa acaagttgaa actg                                              24

<210> SEQ ID NO 39
<211> LENGTH: 23
<212> TYPE: DNA
<213> ORGANISM: Homo sapiens -continued

```
<400> SEQUENCE: 39
tcatctgtca ggtggattgc tgt                                           23

<210> SEQ ID NO 40
<211> LENGTH: 30
<212> TYPE: DNA
<213> ORGANISM: Homo sapiens

<400> SEQUENCE: 40
ggggcggggc tgactatatt gattacatcg                                    30

<210> SEQ ID NO 41
<211> LENGTH: 28
<212> TYPE: DNA
<213> ORGANISM: Homo sapiens

<400> SEQUENCE: 41
ggggcgggcg gctatgtaac atttttga                                      28

<210> SEQ ID NO 42
<211> LENGTH: 23
<212> TYPE: DNA
<213> ORGANISM: Homo sapiens

<400> SEQUENCE: 42
gcgggcgggg ccctggacag gcc                                           23

<210> SEQ ID NO 43
<211> LENGTH: 26
<212> TYPE: DNA
<213> ORGANISM: Homo sapiens

<400> SEQUENCE: 43
ggggcgggcg tacctgtatt ccttgc                                        26

<210> SEQ ID NO 44
<211> LENGTH: 24
<212> TYPE: DNA
<213> ORGANISM: Homo sapiens

<400> SEQUENCE: 44
gacctgcagc aagggagtca gaag                                          24

<210> SEQ ID NO 45
<211> LENGTH: 24
<212> TYPE: DNA
<213> ORGANISM: Homo sapiens

<400> SEQUENCE: 45
agaagccagc aatctcagcc actg                                          24

<210> SEQ ID NO 46
<211> LENGTH: 27
<212> TYPE: DNA
<213> ORGANISM: Homo sapiens

<400> SEQUENCE: 46
ggcggcgcgt ccctattcc ctgcttg                                        27

<210> SEQ ID NO 47
<211> LENGTH: 28
<212> TYPE: DNA
<213> ORGANISM: Homo sapiens
```

-continued

<400> SEQUENCE: 47
ggggcgggcg gacacccctc aagttcct                                         28

<210> SEQ ID NO 48
<211> LENGTH: 820
<212> TYPE: DNA
<213> ORGANISM: Homo sapiens

<400> SEQUENCE: 48
tggggatcca agttcccctc tctccacctg tgctcacctc tcctccgtcc ccaaccctgc      60
acaggcaaga tcgtggacgc cgtgattcag gagcaccagc cctccgtgct gctggagctg     120
ggggcctact gtggctactc agctgtgcgc atggcccgcc tgctgtcacc aggggcgagg     180
ctcatcacca tcgagatcaa ccccgactgt gccgccatca cccagcggat ggtggatttc     240
gctggcgtga aggacaaggt gtgcatgcct gacccgttgt cagacctgga aaaagggccg     300
gctgtgggca gggcgggcat gcgcactttg atcctcccca ccaggtgttc acaccacgtt     360
cactgaaaac ccactatcac caggcccctc agtgcttccc agcctggggc tgaggaaaga     420
cccccccagc agctcagtga gggtctcaca gctctgggta aactgccaag gtggcaccag     480
gaggggcagg gacagagtgg ggccttgtca tcccagaacc ctaaagaaaa ctgatgaatg     540
cttgtatggg tgtgtaaaga tggcctcctg tctgtgtggg cgtgggcact gacaggcgct     600
gttgtatagg tgtgtaggga tggcctcctg tctgtgagga cgtgggcact gacaggcgct     660
gttccaggtc acccttgtgg ttggagcgtc ccaggacatc atcccccagc tgaagaagaa     720
gtatgatgtg gacacactgg acatggtctt cctcgaccac tggaaggacc ggtacctgcc     780
ggacacgctt ctcttggagg tgagcccccaa ccaggatggc                          820